US009005663B2

(12) United States Patent
Raghuraman et al.

(10) Patent No.: US 9,005,663 B2
(45) Date of Patent: *Apr. 14, 2015

(54) METHODS FOR PRODUCING SILVER NANOPARTICLES

(75) Inventors: Kannan Raghuraman, Columbia, MO (US); Kattesh K. Katti, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 2222 days.

This patent is subject to a terminal disclaimer.

(21) Appl. No.: 10/931,174

(22) Filed: Aug. 31, 2004

(65) Prior Publication Data

US 2006/0045916 A1    Mar. 2, 2006

(51) Int. Cl.
| | | |
|---|---|---|
| *A61K 9/14* | (2006.01) | |
| *A61K 33/38* | (2006.01) | |
| *A61K 47/12* | (2006.01) | |
| *A61K 47/14* | (2006.01) | |
| *A61K 47/16* | (2006.01) | |
| *A61K 31/66* | (2006.01) | |
| *B22F 9/24* | (2006.01) | |
| *A61K 9/20* | (2006.01) | |
| *A61K 9/24* | (2006.01) | |
| *B22F 1/00* | (2006.01) | |
| *B82Y 30/00* | (2011.01) | |
| *C22C 5/06* | (2006.01) | |

(52) U.S. Cl.
CPC ............... *A61K 9/14* (2013.01); *A61K 9/2018* (2013.01); *A61K 9/2054* (2013.01); *A61K 9/209* (2013.01); *A61K 33/38* (2013.01); *B22F 1/0022* (2013.01); *B22F 9/24* (2013.01); *B82Y 30/00* (2013.01); *C22C 5/06* (2013.01)

(58) Field of Classification Search
CPC ........ A61K 9/14; A61K 33/38; B22F 1/0022; B22F 9/24; B82Y 30/00
USPC .......... 424/489, 618; 514/114, 784, 785, 788; 75/370
See application file for complete search history.

(56) References Cited

U.S. PATENT DOCUMENTS

| | | | | |
|---|---|---|---|---|
| 3,717,701 | A | * | 2/1973 | Carlson .......................... 423/272 |
| 3,847,279 | A | | 11/1974 | Montgomery |
| 5,541,289 | A | * | 7/1996 | Gilbertson .................... 530/327 |
| 5,948,386 | A | * | 9/1999 | Katti et al. .................... 424/1.77 |
| 6,103,868 | A | | 8/2000 | Heath et al. |
| 6,572,673 | B2 | | 6/2003 | Lee et al. |
| 6,818,199 | B1 | | 11/2004 | Hainfeld et al. |
| 2005/0054613 | A1 | | 3/2005 | Katti et al. ....................... 514/80 |

FOREIGN PATENT DOCUMENTS

WO    WO 03/072053 A2    9/2003

OTHER PUBLICATIONS

P. Raveendran, J. Fu and S. L. Wallen, "Completely 'Green' Synthesis and Stabilization of Metal Nanoparticles", Journal of the American Chemical Society, 2003, 125(46), 13940-13941.*
Neil G. Connely, Ture Damhus, Richard M. Hartshorn and Alan T. Hutton, "Nomenclature of Inorganic Chemistry IUPAC Recommendations 2005", International Union of Pure and Applied Chemistry, 2005, 51-52.*
Yong Shao, Yongdong Jin and Shaojun Dong, "Synthesis of gold nanoplates by aspartate reduction of gold chloride", Chemical Communications, 2004, 1104-1105.*
Pending U.S. Appl. No. 11/219,497, filed Sep. 2, 2005 entitled "Methods and articles for gold nanoparticle production" by Katti, Raghuraman et al.
Jorge Gardea-Torresdey, "Plants with Midas Touch: Formation of Gold Nanoparticles by Alfalfa Plants," University of Texas at El Paso. Believed published circa 2002 on the World Wide Web at: http://www-ssrl.slac.stanford.edu/research/hiqhlights_archive/alfalfa.html.
Beomseok Kim et al., "Tuning the Optical Properties of Large Gold Nanoparticle Arrays," Mat. Res. Soc. Symp. Proc. vol. 676, Materials Research Society (2001).
Beomseok Kim et al., "Self-Organization of Large Gold Nanoparticle Arrays," J. Am. Chem. Soc., 123, 7955-7956 (2001).
Santanu Bhattacharya et al. "Synthesis of gold nanoparticles stabilised by metal-chelator and the controlled formation of close-packed aggregates by them," Proc. Indian Acad. Sci. (Chem. Sci), vol. 115, Nos. 5 & 6. pp. 613-619, (Oct.-Dec. 2003).
"Characterization of Supramolecular $(H_2O)_{18}$ Water Morphology and Water-Methanol $(H_2O)_{15}(CH_3OH)_3$ Clusters in a Novel Prosperous Functionalized Trimeric Amino Acid Host," K. Raghuraman et al., J. Am. Chem. Soc., 125 (23) pp. 6955-6961 (2003).
Volkert, W.A., T.J. Hoffman, "Therapeutic Radiopharmaceuticals," Chem. Rev. (Review) 99 (9); 2269-2292, 1999.
Balogh, Lajos P. Shraddha S. Nigavekar, Andrew C. Cook, Leah Minc, Khan, Mohamed K., "Development of dendrimer-gold radioactive nanocomposites to treat cancer microvasculature," PharmaChem 2(4): 94-44, 2003.
Kandikere Ramaiah Prabhu et al. "De novo synthetic design for air-stable *bis* primary phosphines: Synthetic, catalytic and biomedical motifs," Special Section: Non-Metal Chemistry; Current Science, vol. 78, No. 4, Feb. 25, 2000.
Walter W. Weare, et al., "Improved Synthesis of Small ($d_{CORE}$≈1.5nm) Phosphine—Stabilized Gold Nanoparticle," 2000 Chemical Society, Published on Web Dec. 27, 2000, pp. 12890-12891.
Suresh K. Bhargava, et al. "Gold Nanoparticle Formation During Bromoaurate Reduction by Amino Acids," 2005 American Chemical Society, Published on Web May 24, 2005, pp. 5949-5956.

(Continued)

*Primary Examiner* — John Pak
*Assistant Examiner* — Nathan W Schlientz
(74) *Attorney, Agent, or Firm* — Greer, Burns & Crain, Ltd.

(57) ABSTRACT

An exemplary embodiment of the invention is a method for making silver nanoparticles, and includes steps of reacting a silver salt with a phosphene amino acid to make silver nanoparticles. Exemplary phosphene amino acids include trimers, with a particular example being a trimeric amino acid conjugate containing one phosphene group. In an exemplary method of the invention, the silver nanoparticles may be produced in timer periods of less than about 30 minutes, and at temperatures of less than about 40° C. Other methods of the invention are directed to methods for stabilizing silver nanoparticles.

26 Claims, No Drawings

(56) References Cited

OTHER PUBLICATIONS

Marie-Christine Daniel et al., "Gold Nanoparticle: Assembly, Supramolecular Chemistry, Quantum-Size-Related Properties, and Applications Toward Biology, Catalysis, and Nanotechnology," 2004 American Chemistry Society, Published on Web Dec. 20, 2003, pp. 293-346.

Lajos P. Balogh, et al., "Development of dendrimer-gold radioactive nanocomposites to treat cancer microvasculature," Pharma Chem. Apr. 2003, pp. 94-98.

Office Action mailed May 26, 2009 in U.S. Appl. No. 11/219,497.

Office Action dated Aug. 6, 2010 from related U.S. Appl. No. 11/219,497, Aug. 6, 2010, John A. Viator.

Yong Shao et al. "Synthesis of gold nanoplates by aspartate reduction of gold chloride." Chem. Comm. Apr. 2004, pp. 1104-1105.

Office Action mailed Jan. 21, 2010 in U.S. Appl. No. 11/219,497.

"Synthesis and Characterization of Stable Aqueous Dispersion of Silver Nanoparticles Through the Tollens Process," Yin et al., J. Mater. Chem., 12, 522-527 (2002).

"Green Technique Makes Silver Nanoparticles," L. Kalaugher, Nanotechweb.org., (Jan. 2004).

"Reduction of Silver Nanoparticles in DMF. Formation of Monolayers and Stable Colloids," I. Pastoriza-Santos et al., Pure Appl. Chem., vol. 72, Nos. 1-2, pp. 83-90 (2000).

"Superlattices of Silver Nanoparticles Passivated by Mercaptan," S. He et al., Journal of Physics D: Applied Physics 34, 3425-3429 (2001).

"Characterization of Supermolecular $(H_2O)_{18}$ Water Morphology and Water-Methanol $(H_2O)_{15}(CH_3OH)_3$ Clusters in a Novel Prosperous Functionalized Trimeric Amino Acid Host," K. Raghuraman et al., J. Am. Chem. Soc., 125 (23) pp. 6955-6961 (2003).

\* cited by examiner

METHODS FOR PRODUCING SILVER NANOPARTICLES

FIELD OF THE INVENTION

A field of the invention is methods for producing silver nanoparticles.

BACKGROUND

Silver nanoparticles have a multitude of valuable applications in the rapidly emerging fields of nanoscience and nanotechnology. Powerful surface plasmon absorption of nanoparticulate silver makes them particularly useful in applications such as biosensors, for example. Silver nanoparticles are a photo-fluorescence marker, which makes them useful for a number of medical and similar applications. They are environmentally and biologically benign. Other exemplary silver nanoparticle applications include smart windows, rewritable electronic paper, electronic panel displays, memory components, and others.

Traditional methods for the production of silver nanoparticles require use of potentially harmful chemicals such as hydrazine, sodium borohydride and dimethyl formamide ("DMF"). These chemicals pose handling, storage, and transportation risks that add substantial cost and difficulty to the production of silver nanoparticles. A highly trained production workforce is required, along with costly production facilities outfitted for use with these potentially harmful chemicals.

These harmful chemicals also make it impractical, if not impossible, to produce silver nanoparticles in-vivo. This limitation results in silver nanoparticles having to be prepared beforehand, sanitized, and then introduced to a body for many medical applications. These extra steps add cost and effort. Also, the complexity of handling silver nanoparticles for these applications further limits their use in such applications.

Another disadvantage of known methods for producing silver nanoparticles relates to the time and heat required for their production. Known methods of production utilize generally slow kinetics, with the result that reactions take a long period of time. The length of time required may be shortened by some amount by applying heat, but this adds energy costs, equipment needs, and otherwise complicates the process. Known methods generally require reaction for 20 or more hours at elevated temperatures of 60°-80 C., for example. The relatively slow kinetics of known reactions also results in an undesirably large particle size distribution and relatively low conversion. The multiple stages of production, long reaction times at elevated temperatures, relatively low conversion, and high particle size distribution of known methods make them costly and cumbersome, particularly when practiced on a commercial scale.

These and other problems with presently known methods for making silver nanoparticles are exacerbated through the relatively unstable nature of the nanoparticles. Using presently known methods, the silver nanoparticles produced have only a short shelf life since they tend to quickly agglomerate.

As a result of these and other problems, unresolved needs remain in the art.

SUMMARY OF THE INVENTION

An exemplary embodiment of a method for making silver nanoparticles includes steps of providing a silver salt, providing a phosphine amino acid, and reacting the silver salt with the phosphene amino acid to make silver nanoparticles. Exemplary phosphine amino acids include trimers, with a particular example being a trimeric amino acid conjugate containing one phosphine group. In exemplary methods of the invention, high conversion is achieved in relatively short times and at relatively low temperatures.

Another exemplary embodiment of the invention is directed to a method for stabilizing silver nanoparticles and includes steps of combining a phosphine amino acid with silver nanoparticles. Preferably the phosphine amino acid is a trimeric amino acid conjugate containing one phosphine group.

DESCRIPTION OF THE EXEMPLARY EMBODIMENTS

Exemplary methods of the present invention include methods for making silver nanoparticles. Exemplary methods of the invention generally include the steps of reacting a silver salt such as $AgNO_3$ with a phosphine amino acid. Methods of the invention have been discovered to offer numerous and valuable advantages over the prior art. For example, the silver salt and phosphine amino acid reactants are environmentally and biologically benign materials that do not require special handling or storage. Silver nanoparticles may be produced through methods of the invention in time periods as short as 5 mins. or less and at room temperature. These and other advantages will be apparent to those skilled in the art when considering the detailed description of exemplary methods of the invention that follow.

A method of the invention includes reacting a silver salt with a phosphene amino acid, with one particular exemplary method including the steps of performing the reaction:

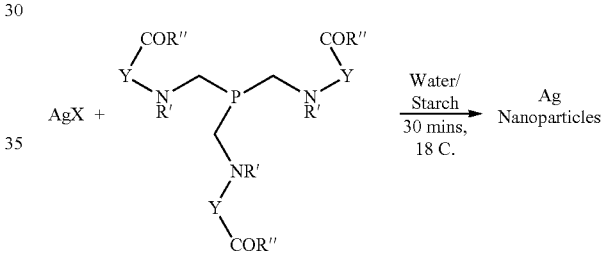

where:
  X=OH, Cl, Br, I or $NO_3$
  R'=Hydrogen, alkyl ($C_1$-$C_6$), or amino protecting group
  R"=$OR^A$, $NR^A R^B$ or $R^C$; where $R^A$=$R^B$=hydrogen, alkyl, phenyl, benzyl, or a carboxyl protecting group; or $R^A$=$R^B$=pyrollidino, piperdino, or thiomorpholinno ring; and $R^C$=alkyl, phenyl or benzyl
  Y=Residue of an amino acid.

Although a trimer amino acid is illustrated and is preferred, a dimer, polymer, or a monomer is also contemplated for use.

The phosphine amino acid is preferably a conjugate amino acid. A particular phosphine amino acid found to be useful in methods of the invention is a trimer amino acid conjugate that contains trimeric alanine and one phosphine group ("TAAC"):

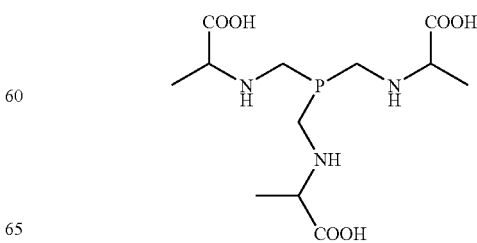

TAAC is described in WIPO International Application No. PCT/US03/05678, Publication No. WO 03/072053, "Compounds for treatment of copper overload," with inventors Katti, Kavita K.; Kannan, Raghuraman; Casteel, Stan W.; Katti, Kattesh V; as well as in "Characterization of Supramolecular ($H_2O_{18}$ Water Morphology and Water-Methanol $(H_2O)_{15}(CH_3OH)_3$ Clusters in a Novel Phosphorus Functionalized Trimeric Amino Acid Host," by Raghuraman, K.; Katti, K. K.; Barbour, L. J.; Pillarsetty, N.; Barnes, C. L.; Katti, K. V.; J. Am. Chem. Soc.; 2003; 125(23); 6955-6961. Preferably at least about 1 mole of trimeric phosphine amino acid is provided per five moles of silver salt. For dimeric phosphine amino acid, preferably at least about one mole of dimer phosphine amino acid is provided per three moles of silver salt, and preferably at least about one mole of monomer phosphine amino acid per two moles of silver salt.

The reaction for the formation of silver nanoparticle is quantitative. The reaction preferably proceeds with at least about 98% formation of silver nanoparticles. There are substantially no byproducts—the phosphine amino acid is oxidized during the reaction to yield a corresponding oxide, which is further consumed for assisting the conversion of the silver salt to Ag nanoparticles. It is believed that the reduction of silver salt is initiated by phosphine, and that the phosphine in turn is oxidized to phosphine oxide. After the initial step, and when using TAAC, the aminocarboxylates in the TAAC oxide serve as the reducing agent to reduce silver salt to silver nanoparticles.

Phosphine amino acids useful in methods of the invention, with TAAC being one example, are environmentally and biologically benign compounds that are stable and easily handled. As such, their use offers substantial advantages over methods of the prior art that require hazardous, biologically/environmentally unfriendly reactants that are more difficult and costly to store and handle.

To aid the reaction, it is preferred that a solvent such as water is provided, along with a stabilizer such as starch. The reaction proceeds substantially to completion in no more than about 30 mins. at room temperature. It is believed that the reaction between silver salt and TAAC proceeds to completion in less than about 5 mins. at room temperature, and may occur substantially instantaneously. These production times represent a substantial improvement over methods of the prior art that required elevated temperatures and relatively long reaction times. Depending on stirring, temperature, and other conditions, however, other periods of time may be useful to carry out a method of the invention. Time periods of up to about 30 mins. or about 1 hour, for example, may be useful to insure maximum conversion. Some elevation in temperature above room temperature may also be useful to insure maximum completion and to speed reaction times, although high temperatures are not necessary. By way of example, the invention may be practiced at temperatures of less than about 40° C., or less than about 30° C.

Methods of the invention also offer substantial improvements in conversion of silver salt to silver nanoparticles. Conversion to nanoparticles of at least about 70% of the silver contained in the silver salt, for example, may be achieved in time periods of less than about 1 hour, in less than about 30 mins, or even in less than about 5 mins. depending on conditions that include concentrations of reactants present, temperature, stirring, and the like. Higher conversions are also possible in methods of the invention, with at least about 90% conversion or 98% more preferred, and in time periods of less than about 30 mins, and more preferably less than about 5 mins. It will be appreciated that the practice of the present invention at relatively low temperatures, short reaction times, and high conversion rates offers important advantages and benefits over the prior art.

Still another valuable advantage of methods of the invention is that the size distribution of resultant silver nanoparticle is relatively tightly defined, and can be at least partially tuned. By way of example, at least about 80% of the silver nanoparticles produced through a method of the invention may have a size range of between about 3-5 nm, while in another method of the invention at least about 80% may be between about 10-20 nm. In general, silver nanoparticles of size 3-30 nm are potentially useful for many medicinal and industrial applications. Methods of the present invention may be practiced to deliver at least about 80%, and more preferably at least about 90% silver nanoparticles having this size.

Desired size ranges may be achieved by varying the concentration of phosphine amino acid present. Taking TAAC as an example, it includes molecular cavities of about 5 nm in size. To increase the number of small sized silver nanoparticles, the amount of TAAC present is increased. Silver nanoparticles are then formed primarily in the cavities. To increase the number of large particle size silver nanoparticles, the amount of TAAC may be decreased to result in a relatively high amount of small particles. When less TAAC is present, a greater proportion of silver nanoparticles are formed on the surface of the TAAC as opposed to in the 5 nm cavities, resulting in a larger average particle size. Empirical testing can be performed to determine required amounts of phosphine amino acid present to yield a desired size range of silver nanoparticles.

It will be appreciated that methods of the invention thereby provide important and valuable benefits over the prior art. For example, because silver nanoparticles can be produced at room temperature, in short periods of time, at high conversion rates, and without the need for hazardous or environmentally/biologically unfriendly reactants, methods of the invention are particularly well suited to in-vitro and in-vivo practice. Silver nanoparticles may be made, for example, in a living organism such as a mammal. By way of example, it may be desirable to make use of the marking or tracing properties of silver nanoparticles for medicinal, research, or other purposes in a human being or an animal. In such cases, a silver salt could be dispersed in an area of interest (during a surgery on an organ, for instance), with a phosphine amino acid solution then introduced in the area. Silver nanoparticles would result. Likewise, a patient might ingest one or both of the reactants so that silver nanoparticles would be produced in the mouth, throat, stomach, or digestive tract as desired. Further, it may be practical to rely on the phosphine amino acids present in proteins to produce silver nanoparticles by introducing a silver salt.

Other applications in which methods of the invention may find utility is military or commercial applications in which it is desired to produce silver nanoparticles quickly, on-site in the field and through a simple procedure. A soldier in combat or a field service technician, for instance, could potentially tear open a two-compartment foil packet with a small amount of an $AgNO_3$ solution in one compartment and a small amount of TAAC in the second. Combining the two materials in an area of interest would produce silver nanoparticles there for later tracking or detection. Also, benefits of the invention including high conversion rates, low reaction temperatures, relatively uniform particle distribution size, and easily handled materials lend themselves well to economical large-scale commercial production and storage.

It has also been discovered that the phosphine amino acid solutions used to make silver nanoparticles through methods of the invention provide a substantially improved storage medium for storing the nanoparticles. Silver nanoparticles may be stabilized (or passivated) by (i) phosphine oxide (e.g., TAAC oxide), (ii) aminocarboxylates (e.g., amino acids from TAAC), and (iii) hydroxyl groups present in starch. Stabilization occurs when weak functional groups from any of these sources bind silver nanoparticles. These weakly bound functional groups can also be easily exchanged with donor ligands such as thiols and/or amines. Amines and/or thiols bearing proteins (or aminoacids) can be bioconjugated to silver nanoparticles by this method. The nanoparticles may be stored for periods of weeks or months without appreciable agglomeration. By way of particular example, silver nanoparticles made through a method of the invention were stored for a period of 2 weeks and for a period of 6 mos. in the TAAC solution with minimal to no agglomeration.

In order to further describe the present invention, detailed exemplary procedures for making silver nanoparticles are presented.

Exemplary Procedure #1

0.1875 gm of starch was added to 50 ml DI water and heated to about 100° C. to dissolve the starch In a separate container, 0.0337 gm of TAAC was dissolved in 1 ml DI water.

A silver salt solution was prepared at room temperature by dissolving 0.039 gm of $AgNO_3$ in 1 ml of DI water.

In a separate container, 100 µl of the silver salt solution was added to 6 ml of the starch solution with stirring at room temperature.

20 µl of the TAAC solution was added to $AgNO_3$/starch solution with stirring at room temperature. The color changes to yellow-brown immediately.

Stirring was continued for about 30 minutes.

This exemplary process of the invention resulted in the production of silver nanoparticles having a size in the range of 10 nm. The nanoparticles were stored in the reaction medium, which contains TAAC oxide, amino carboxylates of TAAC, and hydroxyl groups of starch in DI water, and found stable for more than 30 days.

Exemplary Procedure #2:

A saturated solution of starch was prepared by heating 50 ml of DI water containing 0.1875g of Starch.

In separate vials, 1M solutions of TAAC and silver nitrate were prepared in DI water.

In a fresh 20 ml sample vial equipped with a magnetic stirrer, 6 ml of the saturated solution of starch was added, followed by 100 µl of 1M solution of $AgNO_3$.

20µl of 1M TAAC solution was added to the $AgNO_3$/Starch solution slowly. The color changes to yellow-brown immediately.

Stirring was continued for 30 minutes.

Other embodiments of the invention are directed to methods for stabilizing silver nanoparticles. One exemplary method includes steps of combining a phosphine amino acid with silver nanoparticles to stabilize the silver nanoparticles. The phosphine amino acid is preferably any of those described above, with monomers, dimers, and trimers being examples. A preferred example is TAAC. Preferably at least about 1 mole of TAAC is provided per mole of silver nanoparticles. At least about 3 moles of dimer phosphine amino acid, and at least about 2 moles of monomer amino acid are provided per mole of silver nanoparticles.

While specific embodiments of the present invention have been shown and described, it should be understood that other modifications, substitutions and alternatives will be apparent to one knowledgeable in the field involved. For example, while methods of the invention have been described using a particular sequence of steps, it will be appreciated that unless specifically noted other sequences may be possible. Also, it will be appreciated that in some circumstances a corresponding salt may be used in place of an acid—it will be appreciated that as used herein the term "acid" encompasses corresponding salts. Such modifications, substitutions and alternatives can be made without departing from the spirit and scope of the invention, which should be determined from the appended claims. Various features of the invention are set forth in the appended claims.

The invention claimed is:

1. A method for producing silver nanoparticles, the method comprising the steps of:
   providing a silver salt;
   combining said silver salt with starch and at least one solvent;
   providing a phosphine amino acid including three alanines bound to a phosphorous center via a NCH2 bond with the following chemical formula

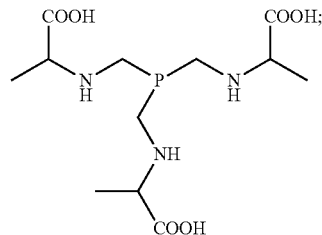 [SMILES: CC(NCP(CNC(C)C(=O)O)CNC(C)C(=O)O)C(=O)O]

and,
   reacting said silver salt with said phosphine amino acid to make silver nanoparticles with a uniform predetermined size and shape that are non-toxic, biologically benign and suitable for use in biologic applications and wherein the size of the silver nanoparticles is controlled by selecting a concentration of said phosphine amino acid.

2. The method of claim 1 wherein the step of reacting said silver salt with said phosphine amino acid to make silver nanoparticles is performed at a temperature of less than 40° C.

3. The method of claim 1 wherein the step of reacting said silver salt with said phosphine amino acid to make silver nanoparticles is performed at a temperature of less than 30° C.

4. The method of claim 1 wherein the step of reacting said silver salt with said phosphine amino acid to make silver nanoparticles is performed at room temperature.

5. The method of claim 1 wherein the step of reacting said silver salt with said phosphene amino acid converts at least 70% of the silver in said silver salt into said silver nanoparticles and is performed in a time period of less than 1 hour.

6. The method of claim 1 wherein the step of reacting said silver salt with said phosphine amino acid converts at least 70% of the silver in said silver salt into said silver nanoparticles and is performed in a time period of less than 30 mins and at room temperature.

7. The method of claim 6 wherein said time period is less than 5 minutes.

8. The method of claim 1 wherein the step of reacting said silver salt with said phosphine amino acid converts at least 98% of the silver in said silver salt into said silver nanoparticles and is performed in a time period of less than 30 mins.

9. The method of claim 1 wherein the step of reacting said silver salt with said phosphine amino acid creates silver nanoparticles at least 80% of which have a size between 10-20 nm.

10. The method of claim 1, wherein the step of providing a phosphine amino acid includes providing a greater amount of said phosphine amino acid if a relatively small silver nanoparticle size is desired, and providing a smaller amount of said phosphine amino acid if a relatively large silver nanoparticle size is desired.

11. The method of claim 1 wherein said silver salt comprises silver nitrate.

12. The method of claim 1 and further including the step of storing said silver nanoparticles for a period of at least 2 weeks without agglomeration of said nanoparticles.

13. The method of claim 12 wherein said period is at least 6 months.

14. The method of claim 1 wherein the method is carried out within a living organism.

15. The method of claim 14 wherein said living organism is a mammal.

16. The method of claim 14 wherein said living organism is a human being, and wherein the step of reacting a silver salt with a phosphine amino acid further includes introducing said silver salt and said phosphine amino acid to a selected area of said human being during a surgical procedure.

17. The method of claim 1 wherein the step of reacting said silver salt with said phosphine amino acid comprises reacting at least 1 mole of said phosphine amino acid per 3 moles of said silver salt.

18. The method of claim 1 wherein the step of reacting said silver salt with said phosphine amino acid comprises reacting at least 1 mole of said phosphine amino acid per 5 moles of said silver salt.

19. The method of claim 1 wherein the step of reacting said silver salt with said phosphine amino acid to make silver nanoparticles is performed at a temperature of less than 30° C. to convert at least 80% of said silver in said silver salt to the silver nanoparticles within 30 mins.

20. The method of claim 1, wherein said phosphine amino acid and said silver salt are reacted in the molar ratio 1:5.

21. A method for producing silver nanoparticles, the method comprising the steps of:
providing a silver salt;
providing a phosphine amino acid, wherein said phosphine amino acid comprises:

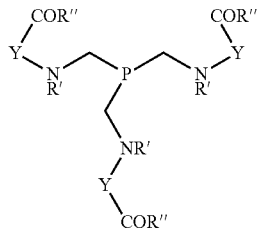

where:
R'=Hydrogen, alkyl (C$_1$-C$_6$), or amino protecting group;
R"=OR$^A$, NR$^A$R$^B$ or R$^C$;
R$^A$=R$^B$=hydrogen, alkyl, phenyl, benzyl, a carboxyl protecting group, pyrollidino, piperdino, or thiomorpholinno ring;
R$^C$=alkyl, phenyl or benzyl; and
Y=CHR, wherein R represents a side chain specific to each amino acid;

combining starch and at least one solvent with said silver salt and said phosphine amino acid; and
reacting said silver salt with said phosphine amino acid to make silver nanoparticles that are non-toxic, biologically benign and suitable for use in biologic applications.

22. The method of claim 21, wherein said phosphine amino acid and said silver salt are reacted in the molar ratio 1:5.

23. A method for producing silver nanoparticles, the method comprising the steps of:
dissolving starch in water to form a starch solution;
dissolving in water to form a phosphine amino acid solution a trimeric amino acid conjugate containing three alanines bound to a phosphorous center via a NCH$_2$ bond with the following chemical structure:

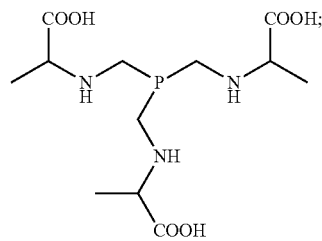 [SMILES: CC(NCP(CNC(C)C(=O)O)CNC(C)C(=O)O)C(=O)O]

dissolving a silver salt in water to form a silver solution;
combining at least a portion of said silver salt solution with at least a portion of said starch solution with stirring to form a silver salt starch solution; and,
combining at least a portion of said phosphine amino acid solution with said silver salt starch solution at a temperature of less than 40° C. with stirring to form silver nanoparticles in less than 30 mins, wherein said silver nanoparticles are non-toxic, biologically benign and suitable for use in biologic applications.

24. The method of claim 23, wherein said phosphine amino acid and said silver salt are reacted in the molar ratio 1:5.

25. A method for storing silver nanoparticles comprising the steps of:
providing silver nanoparticles;
providing a phosphine amino acid including three alanines bound to a phosphorous center via a NCH2 bond with the following chemical structure:

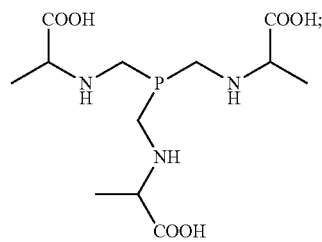 [SMILES: CC(NCP(CNC(C)C(=O)O)CNC(C)C(=O)O)C(=O)O]

and,
combining said silver nanoparticles with said phosphine amino acid and storing said nanoparticles together with said phosphine amino acid.

26. The method of claim 25 and further including the step of storing said silver naoparticles for a period of at least 2 weeks without agglomeration.

* * * * *